Figure 1:
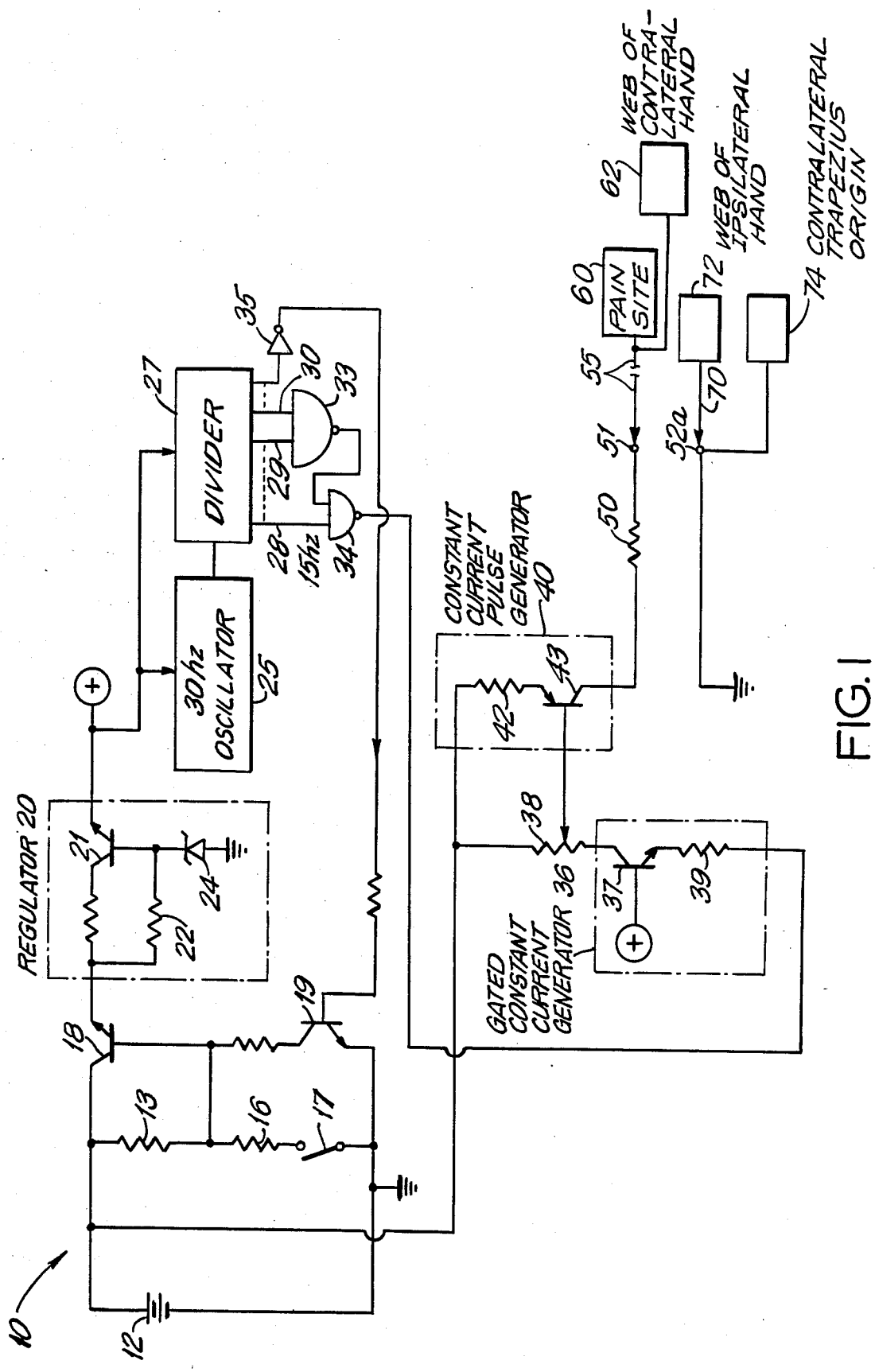

United States Patent [19]

Liss et al.

[11] Patent Number: 4,627,438

[45] Date of Patent: * Dec. 9, 1986

[54] ELECTRONIC MIGRAINE MODULATOR APPARATUS AND METHODOLOGY

[75] Inventors: Saul Liss; Bernard Liss, both of Glen Rock, N.J.

[73] Assignee: Pain Suppression Labs, Inc., Elmwood Park, N.J.

[*] Notice: The portion of the term of this patent subsequent to Nov. 5, 2002 has been disclaimed.

[21] Appl. No.: 640,104

[22] Filed: Aug. 13, 1984

Related U.S. Application Data

[63] Continuation-in-part of Ser. No. 569,476, Jan. 9, 1984, Pat. No. 4,550,733.

[51] Int. Cl.$^4$ ............................................. A61N 1/36
[52] U.S. Cl. ................................................. 128/419 R
[58] Field of Search .................... 128/419 R, 421–423

[56] References Cited

U.S. PATENT DOCUMENTS

| | | | |
|---|---|---|---|
| 2,004,751 | 6/1935 | Fischer et al. | 128/423 R |
| 3,640,284 | 2/1972 | De Langis | 128/422 |
| 3,791,373 | 2/1974 | Winkler et al. | 128/422 |
| 3,902,502 | 9/1975 | Liss et al. | 128/422 |
| 3,991,744 | 11/1976 | Goodfield | 128/664 |
| 4,109,660 | 8/1978 | Nesmeyanov et al. | 128/419 R |
| 4,155,366 | 5/1979 | Di Mucci | 128/421 |
| 4,232,680 | 11/1980 | Hudleson et al. | 128/422 |
| 4,233,986 | 11/1980 | Tennenbaum | 128/421 |

FOREIGN PATENT DOCUMENTS

| | | | |
|---|---|---|---|
| 2500309 | 8/1982 | France | 128/422 |
| 605603 | 5/1978 | U.S.S.R. | 128/421 |

OTHER PUBLICATIONS

Staodynamics, Inc., "TENS for Pain Control", Publication No. 4,405,884 ©1983.

*Primary Examiner*—William E. Kamm
*Assistant Examiner*—Mitchell J. Shein
*Attorney, Agent, or Firm*—Stephen B. Judlowe

[57] ABSTRACT

Migraine modulator apparatus and methodology employs a transcutaneous electronic wave to reduce and control migraine headaches. A first positive contact electrode is placed at the pain site and a second positive contact is placed at the web of the contra-lateral hand; a first negative contact is placed at the contra-lateral trapezius origin, and a second negative contact electrode is placed at the web of the ipsilateral hand. An electronic current wave comprising relatively high frequency pulses with a low frequency amplitude modulation is then applied between the positive and negative electrodes.

3 Claims, 5 Drawing Figures

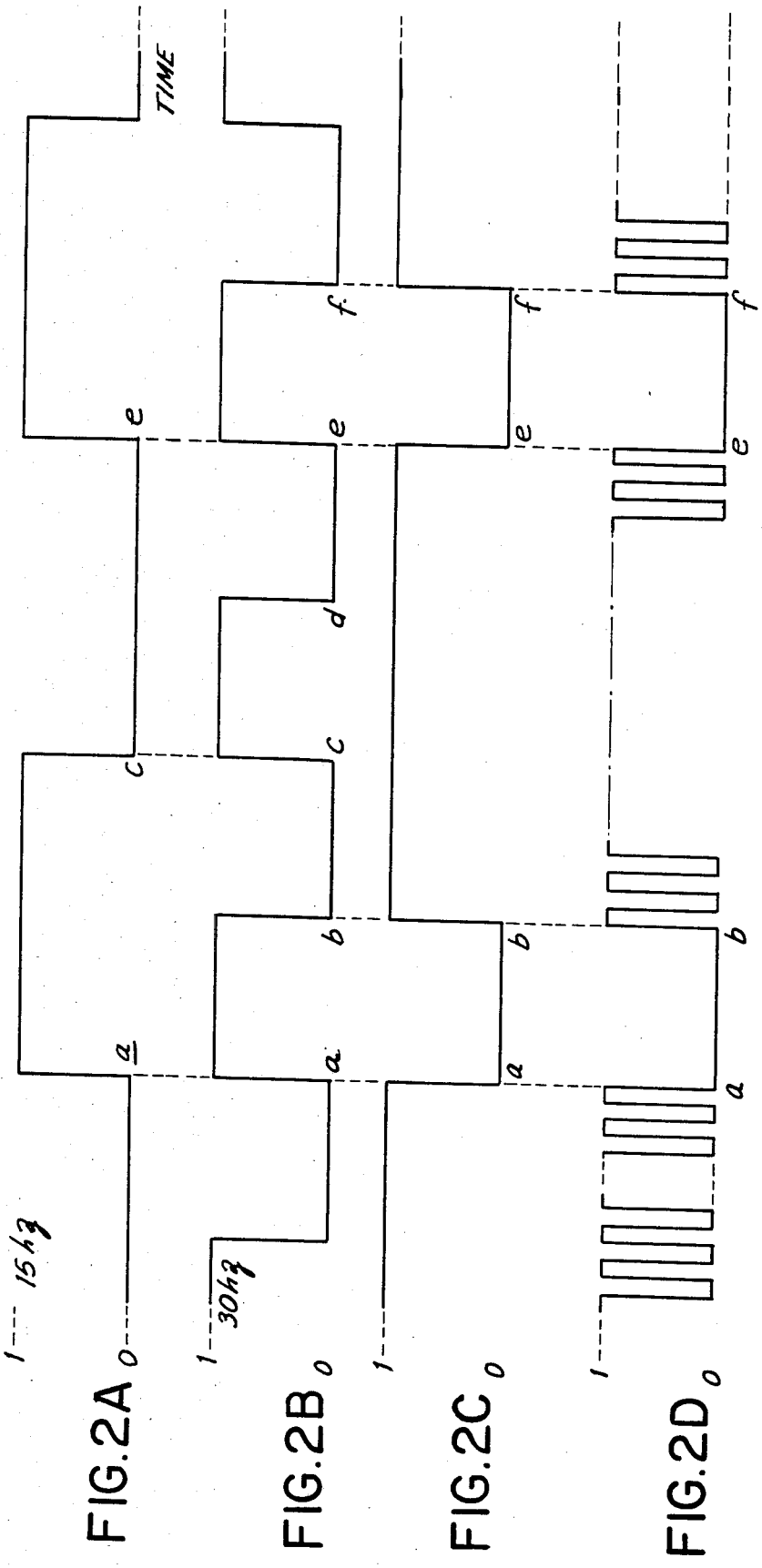

ELECTRONIC MIGRAINE MODULATOR APPARATUS AND METHODOLOGY

This application is a continuation-in-part of U.S. application Ser. No. 569,476 filed Jan. 9, 1984; now U.S. Pat. No. 4,550,733.

DISCLOSURE OF THE INVENTION

This invention relates to electronic pain suppression apparatus and methodology and, more specifically, to migraine modulator apparatus and procedure for reducing or controlling migraine headaches.

It is an object of the present invention to provide migraine modulator apparatus and methodology for treating migraine headaches.

More specifically, an object of the present invention is the electronic treatment of migraine headaches in a safe, efficient and rapid manner to reduce or control the headache and alleviate pain associated with the disease.

It is a further object of the present invention to provide electronic transcutaneous electronic nerve stimulating equipment operative at very low, milliampere current levels, which relieves perceived pain, and treats migraine headaches.

The above and other objects and features of the instant invention are realized in a specific illustrative migraine modulator and methodology which employs a transcutaneous electronic wave to reduce or control migraine headaches. A first positive contact electrode is placed at the pain site and a second positive contact is placed at the web of the contra-lateral hand; a first negative contact is placed at the contra-lateral trapezius origin, and a second negative contact electrode is placed at the web of the ipsilateral hand. An electronic current wave comprising relatively high frequency pulses with a low frequency modulation is then applied from the positive to the negative electrodes.

The above and other features and advantages of the instant invention will become more clear from the following detailed description of a specific illustrative embodiment thereof, presented hereinbelow in conjunction with the accompanying drawing, in which:

FIG. 1 is a schematic diagram of electronic migraine modulator apparatus embodying the principles of the present invention; and FIGS. 2A through 2D are wave forms illustrating the operation of the FIG. 1 apparatus.

A migraine headache is said to be a vascular headache. A dilation of a blood vessel on one side of the head results in pain, which may be triggered by stress, biochemical changes in the body, or by an allergic reaction to food or drink.

The apparatus of the instant invention has been found to relieve the symptoms of migraine headaches with a relatively low level current and without chemical intervention.

To illustrate performance of the instant invention in overview, the apparatus of FIG. 1 is utilized to treat the symptoms associated with the diseased state of a patient who is suffering from migraine headaches. A first positive contact electrode 60 (FIG. 1) is placed at the site of the pain, a second positive contact electrode 62 (FIG. 1) is placed on the web of the contra-lateral hand. A first negative contact electrode 74 (FIG. 1) is placed on the contra-lateral trapezius origin and a second negative contact electrode 72 (FIG. 1) is placed at the web of the ipsilateral hand. The treatments should be from fifteen to twenty minutes.

An electronic wave (depicted in FIG. 2D) is applied from the positive electrodes 60 and 62 to the electrodes 72 and 74 which are connected on common. The wave form of FIG. 2D comprises a low level (less than 4 milliamperes) pulse train of relatively high frequency, e.g., between 12 and 20 khz modulated in amplitude by a relatively low frequency wave in the range of 8 to 20 hz. The low frequency wave is preferably non-symmetrical (that shown in FIG. 2D), for example, characterized by a 3:1 duty cycle, being on three-fourths of the time and off one-fourth of the recurring period. For concreteness only and without limitation, it will hereinafter be assumed that the high frequency pulse occurs at a 15 khz rate and 1-1.5 m.a. level, while being subject to a 15 hz modulation with a 3:1 duty factor.

I have found that the wave of FIG. 2D is effective to block the pain perceived and relieve the migraine headache. The particular mechanism causing elimination of the pain associated with migraine headaches is believed to follow from the increase in serotonergic levels at the medullary site which can increase beta-endorphin in response to the low frequency modulation envelope introduced into the body; the high frequency wave constituent serves as a transcutaneous carrier for the low frequency modulation, thereby increasing the presence of the body's own opiate control bio-chemical at the periaqueductal gray of the brain. Serotonin has been accepted as the bio-chemical in the descending pathways of the brain, whose signals are involved with the inhibitory or balancing characteristic of the pain signal. Therefore, if pain is a result of an imbalance of the bio-chemicals in the body and the result of an excitatory factor involving the substance "P" ascending pathways which is not counteracted or inhibited by a balancing signal from the descending pathways of the brain which use serotonin as the neural transmitter. Thus, the serotonin may prevent the transmission of a painful signal. Therefore, we conclude that increasing the serotonin level, which does occur with the use of the "Migraine Modulator" can in four out of five cases reduce the pain of migraine headache.

Sensitization is a neural process wherein the body requires less stimulation at a time subsequent to initiating stimulation to perceive a particular sensation. The neuro-transmitter serotonin is also implicated in the neural process of sensitization. By increasing the transmission of a signal across the synapse through an increase in serotonin (the basis of sensitization) that signal can provide pain control. Therefore, if a person utilizes the "Migraine Modulator" for specific pain control and sensitization occurs we can expect pain control. If it does not occur, then we can also at some subsequent time use the same device transcranially where the contacts are one inch above the ears, red on the right and black on the left, substantially on a line with the hypothalamus where serotonin is used. This provides a central stimulation for enhancing a particular focal application. See Messing R.: Behavioral Effects of Serotonin Neurotoxins: An Overview, *Annals of the New York Academy of Science* 978: 480-496 which supports the idea that the neural process of sensitization occurs when serotonin levels are increased.

The "Migraine Modulator" may work in a variety of ways to increase serotonin or any neuro-transmitter.

1. It may increase the number of serotonin molecules. The evidence of this lies in the fact that, with people who do not benefit with the "Migraine Modulator", the addition of "L" Tryptophan to their diets will increase the effectiveness of the invention. This amino acid, which is the precursor to serotonin, provides the building blocks which may raise the number of serotonin molecules, through the use of the "Migraine Modulator".

2. It may increase the number of serotonin receptor sites.

3. It may be altering the permeability of the nerve tissue to enhance the passage of the calcium ions across the synapse which would improve the information transfer across that particular synapse. See Wai Yiu Cheung: Calmodulin, *Scientific American*, June 1982, pp. 62–70.

While the precise operative mechanism may be the subject of debate, the fact of the migraine pain relief is not.

The FIG. 1 electronic apparatus 10 for generating and applying the wave form of FIG. 2D will now be specifically considered. A battery 12 is connected to a PNP series pass transistor 18 which, in turn, selectively passes the voltage from battery 12 through a voltage regulator 20 to form the positive direct current voltage supply for the apparatus 10 electronics. The unit is first turned on by momentarily closing a power-on switch 17. This applies a low voltage to the base of PNP transistor 18, turning that device on and effectively coupling the potential of battery 12 to a series pass transistor 21 in the voltage regulator 20. Because the final output of a counter or divider chain 27 is initially low on power turn on, the resulting high output of inverter 35 applies a high potential to the base of transistor 19, turning it on and thereby latching PNP transistor 18 to its conductive condition when switch 17 is released. This maintains the electronic apparatus on for a desired period which is determined by the frequency of an oscillator 25 and the division factor of the divider 27, i.e., the period required for the most significant stage of the counter 27 to reach its high or binary "1" state. The switched power supply assures that the electronic apparatus is not inadvertently left on to unduly discharge the battery 12.

The regulated output of battery 12 applied through PNP transistor 18 is converted to a lower regulated value by the regulator 20. Regulator 20 is per se well known and includes the series pass PNP transistor 21 having a constant voltage applied to the base thereof by a Zener diode 24 energized by a resistor 22. The constant potential output of regulator 20, which serves as the supply voltage for much of the remaining electronics of FIG. 1, is the characteristic reverse excitation voltage of Zener diode 24 less about 7/10 of a volt for the base-emitter drop of transistor 21.

As above noted, the active power supply interval for circuit 10 of the drawing is fixed and preset to a specific period. The above-discussed time out circuitry is employed to assure that the unit is not inadvertently left on. Many ways of achieving this result will be readily apparent to those skilled in the art. For example, a variable time out may be provided by employing a switch to connect the input of inverter 35 to varying ones of the more significant stage outputs of the pulse counter chain 27. Yet further, separate electronic or electromechanical timer apparatus, fixed or variable, all per se well known, may be employed to supply a positive potential to the base of transistor 19 for the desired "on" period; and to switch off the base drive to transistor 19, thereby turning off series pass transistor 18, when the desired operative period has passed.

A time base oscillator 25 supplies an input to the pulse counter or divider chain 27. The frequency of oscillator 25 is chosen for convenience to be an integral multiple of the pulse frequency (FIG. 2D) desired for delivery to the patient. For the assumed 15 khz desired frequency, a 30 khz oscillation repetition rate may be usefully employed for oscillator 25, such that the 15 khz signal is derived at a divide-by-two tap 28 of divider chain 27. The 15 khz signal is supplied as one input to a NAND gate 34, the output of which corresponds to the ultimately desired wave of FIG. 2D. Outputs 29 and 30 of divider 27 are supplied as inputs to a NAND gate 33, the output of which is supplied as a second input to the NAND gate 34. The output 29 of divider 27 supplies the 30 hz wave of FIG. 2B (pulse division factor 1,000 at tap 29), while the 15 hz wave of FIG. 2A is supplied at a divider output 30 (divider factor: 2,000). Logic gate 33 generates the output wave of FIG. 2C, being at its high or Boolean "1" value when either of the waves of FIGS. 2A or 2B is low (i.e., preceding the time a, during the interval b-e, - and following time f). Correspondingly, during the periods a-b and e-f when the output at divider 27 taps 29 and 30 are both high, the output of gate 33 is low (Boolean "0" value).

The wave form of FIG. 2C is supplied as one input to the gate 34 together with the 15 khz pulse train at the divide-by-two counter 27 output port 28. Accordingly, the output of NAND gate 34 switches between its high and low state during the periods when the FIG. 2C wave is high, i.e., preceding time a, during the interval b-e, following the time f, and so forth for the recurring pattern illustrated by FIGS. 2A-2D.

The voltage wave form of FIG. 2D is converted to a current in the milliampere range for application to the patient by the following circuitry of FIG. 1. As a first matter, a gated constant current generator 36 passes a gated current (either off or of a fixed value) through a potentiometer 38 under control of the output of the NAND gate 34. When the output of NAND gate is low, a transistor 37 in constant current generator 36 is on and a current substantially given by the positive potential output of regulator 20 (applied to the base of transistor 37) less a 7/10 of a volt base emitter drop for the transistor 37, divided by the resistance value of the resistance 39 in the emitter circuit of transistor 37. The voltage at the variable tap of the potentiometer 38 is supplied to the base of a PNP transistor 43 of a constant current pulse generator 40. The output of pulse generator 40 is a current which switches between its off (zero current) state, and a value given by the voltage at the potentiometer 38 tap, less a diode drop for the emitter-base of transistor 43, divided by the resistance value of resistor 42 connected in the emitter circuit of the PNP device 43. This pulsed current output of pulse generator 40 corresponds in wave form to FIG. 2D, and is at a level, determined by the setting of potentiometer 38, in the low milliampere range. It is this current pulse which is ultimately delivered to the patient to provide the requisite relief of symptoms.

In a typical application the patient is provided with the potentiometer 38. The potentiometer is first turned up so that the administered current pulses provide a noticeable tingling sensation on the patient's skin surface. The patient is then instructed to turn down the potentiometer adjustment until the sensation just disappears. The will provide the amount of transcutaneous electronic stimulation to treat the symptoms associated with the patient's disease. The potentiometer setting may be adjusted by the patient as required.

The current pulses from generator 40 pass through a protective, series limiting resistor 50 to an output terminal 51. It there flows via the lead 55 connected to terminal 51 to the electrode 60 adhered to the pain site and the electrode 62 is placed on the web of the contra-lateral hand. The current transcutaneously passes into the patient, flows through the patient, and returns to electronic ground via the electrode 74 adhered to the contra-lateral trapezius origin and the electrode 72 adhered to the web of the patient's ipsilateral hand. Electrodes 72 and 74 are connected to electronic system ground via lead 70 and apparatus terminal port 52a.

As above noted, the apparatus and methodology of the instant invention treats the pain and other symptoms associated with migraine headaches. The apparatus and methodology has manifest advantages for alleviating the patient's symptoms.

The above-described arrangement and methodology are merely illustrative of the principles of the present invention. Numerous modifications and adaptations thereof will be readily apparent to those skilled in the art without departing from the spirit and scope of the present invention.

EXAMPLE

The historical information which indicates success in reducing migraine headaches using the "Migraine Modulator" is indicated by the work of Colonial Joan Graziano at Walter Reed Army Medical Center where use on sixty-one cases indicated eighty-three percent success and the articles by Doctor Simon Markovitch in "Pain in the Head" and in the presentation he gave to the Neural Electronic Conference at San Marco Island in Florida also indicate success in reducing migraine headaches using our high frequency "Migraine Modulator."

What is claimed is:

1. Electronic migraine modulator apparatus and methodology for employing a transcutaneous electronic wave to reduce and control migraine headaches, first positive contact electrode means being placed at the pain site and a second positive contact means is placed at the web of the contra-lateral hand; a first negative contact is placed at the contra-lateral trapezius origin, and a second negative contact electrode means is placed at the web of the ipsilateral hand, and means for supplying an electronic current wave comprising a high frequency electrical wave bearing a low frequency amplitude modulation to said first and said second electrode.

2. The method as in claim 1, wherein the frequency of said high frequency electrical wave was in the range of 12–20 khz, wherein said low frequency modulation is in the range 8–20 hz, and wherein said wave does not exceed about 4 milliamperes.

3. The method as in claim 1 or 2, wherein said amplitude modulation is non-symmetrical.

* * * * *